(12) United States Patent
Akiyama et al.

(10) Patent No.: US 9,897,579 B2
(45) Date of Patent: *Feb. 20, 2018

(54) METHOD FOR CORRECTING EVOLVED GAS ANALYZER AND EVOLVED GAS ANALYZER

(71) Applicant: HITACHI HIGH-TECH SCIENCE CORPORATION, Tokyo (JP)

(72) Inventors: Hideyuki Akiyama, Tokyo (JP); Kantaro Maruoka, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/356,585

(22) Filed: Nov. 19, 2016

(65) Prior Publication Data

US 2017/0146497 A1 May 25, 2017

(30) Foreign Application Priority Data

Nov. 20, 2015 (JP) ................... 2015-227372

(51) Int. Cl.
*G01N 27/62* (2006.01)
*G01N 30/30* (2006.01)
(Continued)

(52) U.S. Cl.
CPC ..... *G01N 30/7206* (2013.01); *G01N 33/0006* (2013.01); *H01J 49/0027* (2013.01);
(Continued)

(58) Field of Classification Search
CPC ...... G01N 27/624; G01N 27/622; G01N 1/38; G01N 30/7253; G01N 30/30; G01N 30/32;
(Continued)

(56) References Cited

U.S. PATENT DOCUMENTS 4,814,612 A * 3/1989 Vestal ............... G01N 30/7253
250/282
4,883,958 A * 11/1989 Vestal ............... G01N 30/7273
250/281

(Continued)

FOREIGN PATENT DOCUMENTS

JP 2005-106524 A 4/2005
JP 2008-190898 A 8/2008

*Primary Examiner* — David A Vanore
(74) *Attorney, Agent, or Firm* — Maschoff Brennan

(57) ABSTRACT

Disclosed herein is a method for correcting an evolved gas analyzer and the evolved gas analyzer. The method includes: correcting a mass spectrum position to be located at a reference spectrum position, the mass spectrum position corresponding to a mass-to-charge ratio m/z of a mass spectrum of a gas component of a reference sample; calculating a sensitivity correction factor Cs=Ss/S by using an area S and a reference area Ss of a chromatogram, the sensitivity correction factor being used to measure an area of a chromatogram of the gas component of a test sample; and calculating a heating correction factor H=t/ts by using a time t and a reference time ts indicating a maximum peak of the chromatogram about the reference sample, the heating correction factor being used to correct a heating rate of the test sample when measuring the gas component of the test sample.

3 Claims, 9 Drawing Sheets

(51) Int. Cl.
*H01J 37/08* (2006.01)
*G01N 30/72* (2006.01)
*H01J 49/00* (2006.01)
*H01J 49/04* (2006.01)
*H01J 49/10* (2006.01)
*G01N 33/00* (2006.01)
*G01N 30/04* (2006.01)

(52) U.S. Cl.
CPC .......... *H01J 49/0468* (2013.01); *H01J 49/10* (2013.01); *G01N 2030/042* (2013.01)

(58) Field of Classification Search
CPC .......... G01N 30/7213; G01N 30/7273; G01N 30/7286; G01N 30/7293; H01J 49/049; H01J 49/022; H01J 49/04; H01J 49/0445; H01J 49/0409; H01J 49/0422; H01J 49/0486; H01J 49/0495; H01J 49/105; H01J 37/08
USPC .... 250/281, 282, 287, 288, 423 R, 424, 425
See application file for complete search history.

(56) References Cited

U.S. PATENT DOCUMENTS

| | | | |
|---|---|---|---|
| 5,367,163 A * | 11/1994 | Otsuka | H01J 49/105 250/281 |
| 7,928,370 B2 * | 4/2011 | Amirav | H01J 49/049 250/281 |
| 2006/0192103 A1 * | 8/2006 | Landgraf | G01N 27/624 250/287 |
| 2008/0128615 A1 * | 6/2008 | Yamada | H01J 49/0422 250/288 |
| 2012/0326022 A1 * | 12/2012 | Kumano | H01J 49/0495 250/288 |
| 2013/0277547 A1 * | 10/2013 | Sato | G01N 27/624 250/282 |
| 2017/0146497 A1 * | 5/2017 | Akiyama | G01N 33/0006 |
| 2017/0146503 A1 * | 5/2017 | Akiyama | G01N 33/0016 |
| 2017/0148616 A1 * | 5/2017 | Akiyama | H01J 49/0422 |
| 2017/0148617 A1 * | 5/2017 | Akiyama | H01J 49/0422 |

* cited by examiner

METHOD FOR CORRECTING EVOLVED GAS ANALYZER AND EVOLVED GAS ANALYZER

CROSS REFERENCE TO RELATED APPLICATION(S)

This application claims the benefit of Japanese Patent Application No. 2015-227372, filed Nov. 20, 2015, which is hereby incorporated by reference in its entirety into this application.

BACKGROUND OF THE INVENTION

1. Technical Field

The present invention relates generally to a method for correcting an evolved gas analyzer and an evolved gas analyzer, the evolved gas analyzer ionizing gas components evolved by heating a sample to apply mass spectrometry to the gas component, thereby identifying, quantifying, etc. the sample.

2. Description of the Related Art

In order to increase flexibility of resins, plasticizers such as phtalates, etc. are added to the resins. After 2019, four substances of the phtalates will be restricted under the restriction of hazardous substances directive (RoHS). Therefore, it is required to identify and quantify the phtalates in the resins.

The phtalates are volatile substances such that a conventional evolved gas analysis (EGA) is applied to analyze the phtalates. The EGA is a method used to analyze gas components evolved by heating a sample by using a gas chromatograph or using various analyzers applying mass spectrometry, etc.

However, mass spectrometry is highly sensitive such that detection accuracy is high. Therefore, it is required to precisely correct the sensitivity, etc. In addition, a mass spectrometer is a general-purpose analysis device. Therefore, it is required for a user to perform complicated operations such as a sensitivity adjustment or a correction depending on a measurement target.

Therefore, a technology of correcting a mass-to-charge ratio m/z (mass number) of the measurement target by using a mass spectrum of a reference sample is disclosed in Patent Documents 1 and 2.

DOCUMENTS OF RELATED ART (Patent Document 1) Japanese Patent Application Publication No. 2008-190898
(Patent Document 2) Japanese Patent Application Publication No. 2005-106524

SUMMARY OF THE INVENTION

As shown in FIG. 9, a gas component, which is a measurement target, is quantified based on an area S of a chromatogram C. Therefore, it is required to correct or adjust the chromatogram C. The area S of the chromatogram C is influenced by a measured temperature, degradation of an ion source ionizing a gas component, etc. In addition, a shape of the chromatogram (time t indicating a maximum peak of the chromatogram) is influenced by a heating rate (temperature rising rate) of a sample. When the shape of the chromatogram C changes into a chromatogram C', time t changes into time t', and the area S changes into an area S' of the chromatogram C'.

The correction and the adjustment may be performed according to an instruction manual of an analysis device. However, a general correction is not always optimized for analyzing each measurement target. Therefore, an additional correction or adjustment may be required depending on the measurement target. In order to perform the correction and adjustment, professional knowledge or experience, and proper reference substances are required. Consequently, operations are complicated, and thus work efficiency is reduced.

Accordingly, the present invention has been made keeping in mind the above problems occurring in the related art, and an object of the present invention is to provide a method for correcting an evolved gas analyzer and the evolved gas analyzer, the method easily correcting detection sensitivity differences in analysis devices, day-to-day variations thereof, etc., thereby enabling the evolved gas analyzer to quantify a measurement target with high accuracy.

In order to accomplish the above object, the present invention provides a method for correcting an evolved gas analyzer, the evolved gas analyzer including: a heating unit evolving a gas component by heating a test sample; an ion source generating ions by ionizing the gas component evolved by the heating unit; and a mass spectrometer detecting the gas component by applying mass spectrometry to the ions; the method using a reference sample including the gas component as a measurement target and including: correcting a mass spectrum position (m/z value) to be located at a reference spectrum position, the mass spectrum position corresponding to a mass-to-charge ratio m/z of a mass spectrum of the gas component of the reference sample; after the correcting of the mass spectrum position (m/z value), calculating a sensitivity correction factor $C_s=S_s/S$ by using an area S and a reference area $S_s$ of a chromatogram showing an intensity of the gas component of the reference sample at a retention time, the sensitivity correction factor being used to measure an area of a chromatogram of the gas component of the test sample; and calculating a heating correction factor $H=t/t_s$ by using a time t and a reference time $t_s$ indicating a maximum peak of the chromatogram of the gas component of the reference sample, the heating correction factor being used to correct a heating rate of the test sample in the heating unit, when measuring the gas component of the test sample.

According to the method for correcting the evolved gas analyzer, by the correcting of the mass spectrum position, it is possible to correct detection sensitivity differences in analysis devices, day-to-day variations thereof, etc. relative to the mass spectrum position of the gas component. Consequently, it is possible to obtain a precise chromatogram of the gas component.

The area of the chromatogram is influenced by degradation of the ion source ionizing the gas component, measured temperature, etc. Therefore, a sensitivity correction factor is required to be used. The area of the chromatogram about the gas component of the test sample is corrected by using the sensitivity correction factor, thereby precisely quantifying the gas component based on the area of the chromatogram.

In the case of heating the test sample, when the heating rate (temperature rising rate) varies, the shape of chromatogram (time t indicating a maximum peak) also varies, and thus, the area of the chromatogram varies. Therefore, a heating correction factor is required to be used. The heating condition of the heating unit is properly controlled by using the heating correction factor, thereby obtaining a precise chromatogram. Consequently, it is possible to precisely quantify the gas component.

In advance of analyzing a test sample, the corrections using the sensitivity correction factor and the heating correction factor are operated once by using one reference sample, thereby quantifying the measurement target with high accuracy and with a high reproducibility by avoiding detection sensitivity differences in analysis devices as well as day-to-day variations thereof.

When the measurement target includes a plurality of gas components, the method further includes calculating a heating correction factor $H=\Sigma ai \times ti/tsi$ (i: a natural number indicating a gas component i, ai: a well-known heating sensitivity factor of the gas component i, ti: a time indicating a maximum peak of a chromatogram of the gas component i, and tsi: a reference time indicating the maximum peak of the chromatogram of the gas component i).

According to the method for correcting the evolved gas analyzer, when the measurement target includes a plurality of gas components, the gas components may be precisely quantified.

According to another aspect, there is provided an evolved gas analyzer including: a heating unit evolving a gas component by heating a test sample; an ion source generating ions by ionizing the gas component evolved by the heating unit; a mass spectrometer detecting the gas component by applying mass spectrometry to the ions; and a correction processing unit using a reference sample including the gas component as a measurement target, wherein the correction processing unit, which is a computer, corrects a mass spectrum position to be located at a reference spectrum position, the mass spectrum position corresponding to a mass-to-charge ratio m/z of a mass spectrum of the gas component of the reference sample; after the correcting of the mass spectrum position, calculates a sensitivity correction factor $Cs=Ss/S$ by using an area S and a reference area Ss of a chromatogram showing an intensity of the gas component of the reference sample at a retention time, the sensitivity correction factor being used to measure an area of a chromatogram of the gas component of the test sample; and calculates a heating correction factor $H=t/ts$ by using a time t and a reference time ts indicating a maximum peak of the chromatogram of the gas component of the reference sample, the heating correction factor being used to correct a heating rate of the test sample in the heating unit, when measuring the gas component of the test sample.

According to the method for correcting the evolved gas analyzer and the evolved gas analyzer, it is possible to correct detection sensitivity differences in analysis devices, day-to-day variations thereof, etc., thereby quantifying the measurement target with high accuracy. In addition, it is possible to perform a proper correction or adjustment of the evolved gas analyzer depending on the measurement target without professional knowledge or experience.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
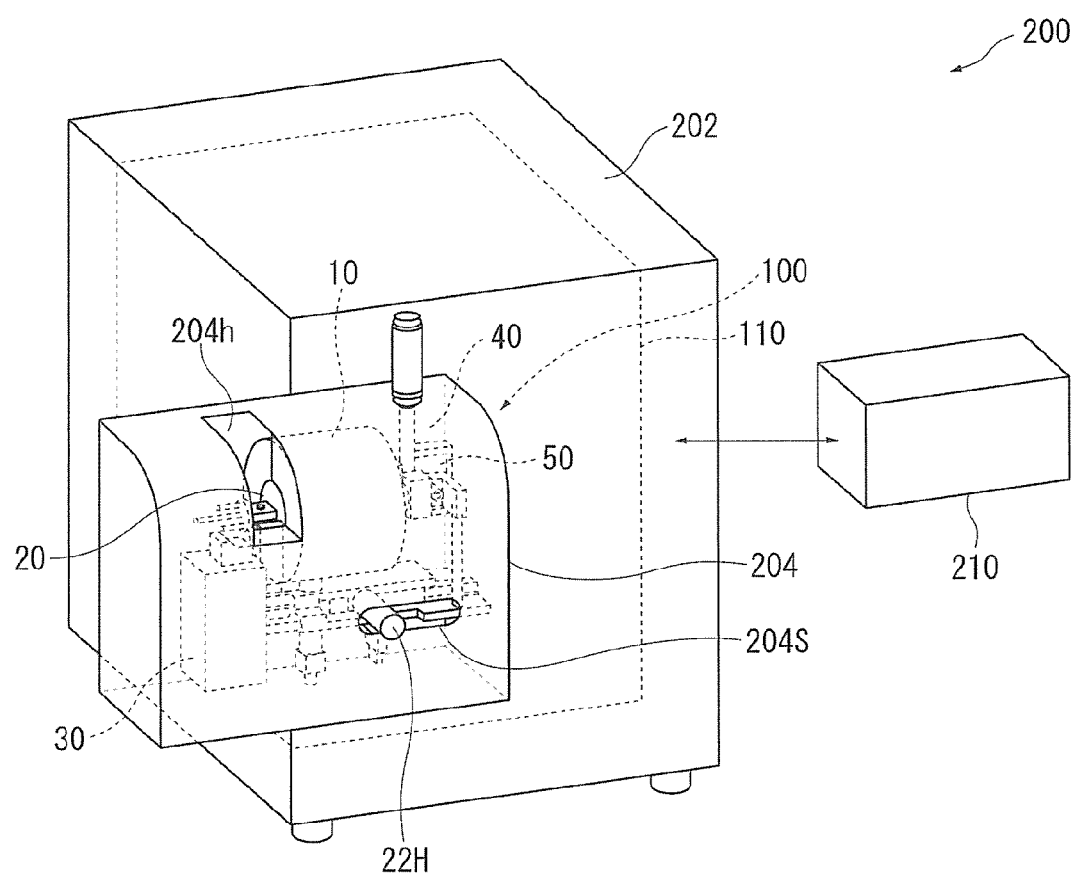
FIG. 1 is a perspective view showing the configuration of an evolved gas analyzer according to an exemplary embodiment of the present invention.
Figure 2:
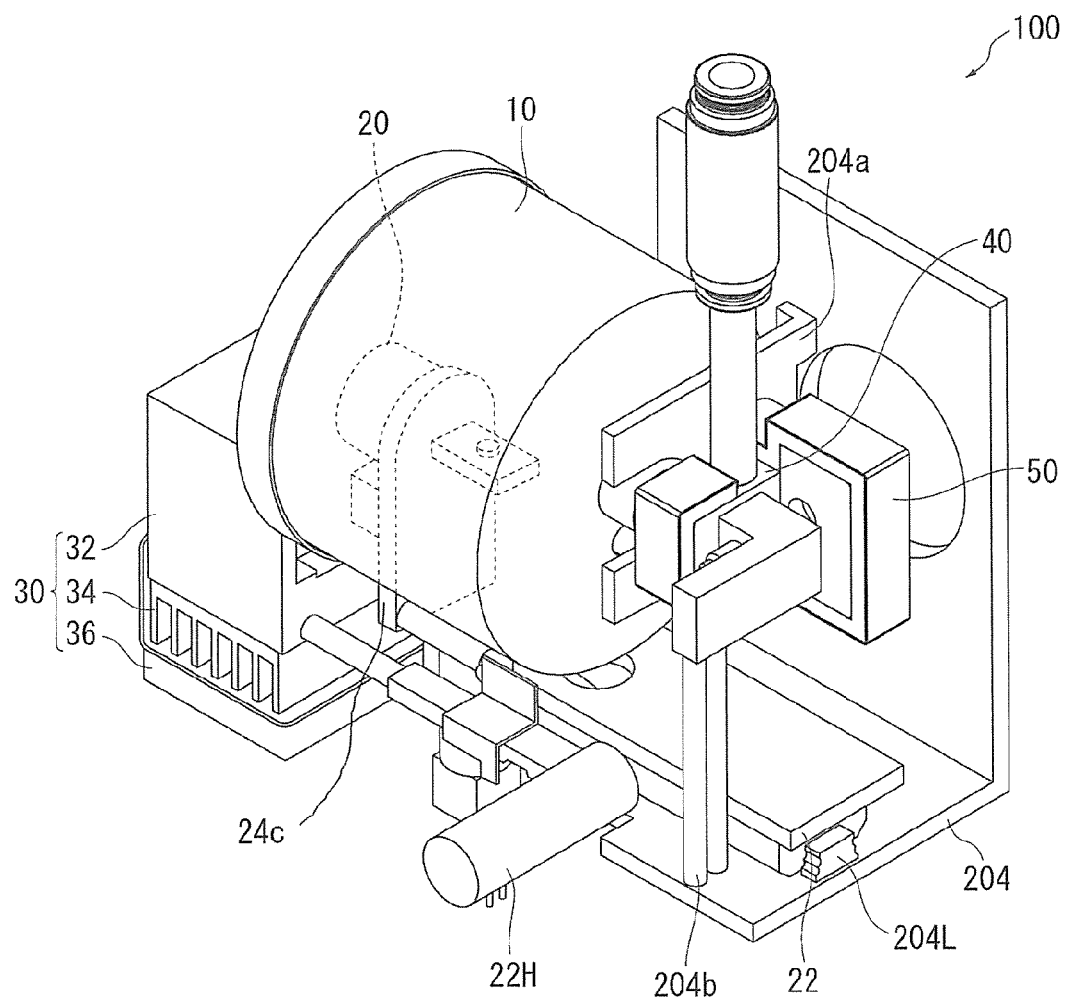
FIG. 2 is a perspective view showing the configuration of a gas evolving unit.
Figure 3:
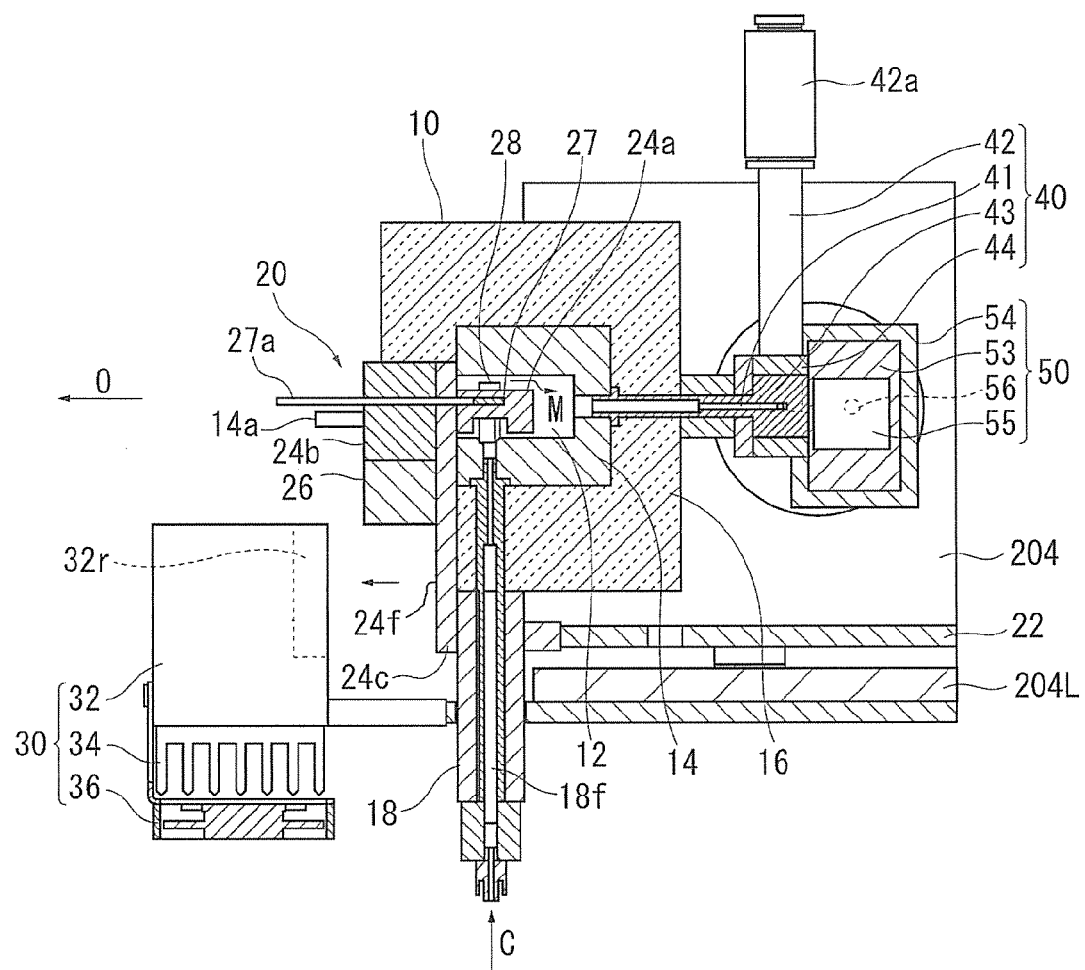
FIG. 3 is a longitudinal sectional view showing the configuration of the gas evolving unit.
Figure 4:
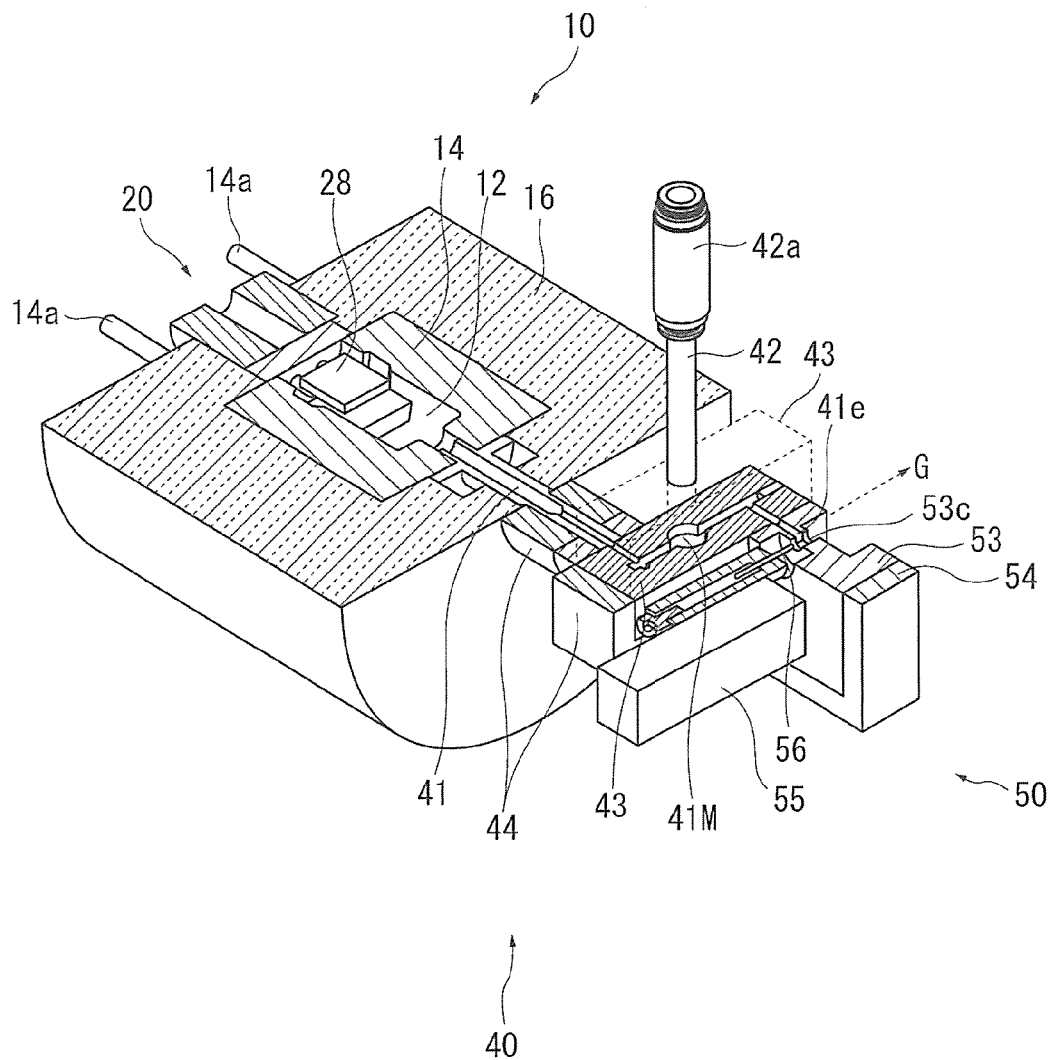
FIG. 4 is a cross-sectional view showing the configuration of the gas evolving unit.

Hereinafter, the exemplary embodiment of the present invention will be described with reference to the accompanying drawings. FIG. 1 is a perspective view showing the configuration of an evolved gas analyzer 200. FIG. 2 is a perspective view showing the configuration of a gas evolving unit 100. FIG. 3 is a longitudinal sectional view showing the configuration of the gas evolving unit 100 on an axis O. FIG. 4 is a cross-sectional view showing the configuration of the gas evolving unit 100 on the axis O.

The evolved gas analyzer 200 includes a body unit 202 that is a housing; an attaching unit 204 for a gas evolving unit, the attaching unit having a box shape and attached at a front surface of the body unit 202; and a computer (control device) 210 controlling the evolved gas analyzer. The computer 210 includes a CPU processing data, a memory unit storing a computer program and data, an input unit such as a monitor, a keyboard, etc. The computer 210 is a correction processing unit in the appended claims.

In the attaching unit 204 for the gas evolving unit, there are a heating furnace (heating unit) 10 having a cylinder shape; a sample holder 20; a cooling unit 30; a splitter 40 splitting gas; and the gas evolving unit 100 having an ion source 50 as assembly. In addition, a mass spectrometer (detecting device) 110 is provided in the body unit 202. The mass spectrometer analyses gas components evolved by heating a sample.

In addition, an opening 204h is provided at an upper surface of the attaching unit 204 for the gas evolving unit, while being provided at a front surface thereof. The sample holder 20 is located at the opening 204h by being moved toward a discharging position that is located at an outside of the heating furnace 10. Therefore, a sample may be supplied on or removed from the sample holder 20 through the opening 204h. In addition, a slit 204s is provided at the front surface of the attaching unit 204. By moving an opening/closing handle 22H exposed to an outside of the attaching unit through the slit, the sample holder 20 is moved into or from the heating furnace 10. Therefore, the sample holder is set at the discharging position, and thus, the sample is supplied on or removed from the sample holder.

In addition, for example, when the sample holder 20 is moved on a movement rail 204L by a stepping motor, etc. controlled by the computer 210, the sample holder 20 may be automatically moved into or from the heating furnace 10.

Hereinafter, the configuration of the gas evolving unit 100 will be described with reference to FIGS. 2 to 5.

First, the heating furnace 10 is attached to an attaching plate 204a of the attaching unit 204 by being parallel to the axis O. The heating furnace includes a heating chamber 12 having a cylinder shape and being opened on the axis O; a heating block 14; and a heat retaining jacket 16.

The heating block 14 surrounds the heating chamber 12, and the heat retaining jacket 16 surrounds the heating block 14. The heating block 14 is made of aluminum, and is heated by electricity from a pair of heating unit heaters 14a extending from the heating furnace 10 to outside in a direction of the axis O as shown in FIG. 4.

In addition, the attaching plate 204a extends in a direction perpendicular to the axis O. The splitter 40 and the ion source 50 are attached to the heating furnace 10. In addition, a supporter 204b extends in a vertical direction of the attaching unit 204, and supports a staying unit 55 of the ion source 50.

The splitter 40 is connected to an opposite side (right side of FIG. 3) of an opening side of the heating furnace 10. In addition, a carrier gas protecting pipe 18 is connected to a lower side of the heating furnace 10. The carrier gas protecting pipe 18 surrounds a carrier gas channel 18f connected to a lower surface of the heating chamber 12. Carrier gas C is introduced into the heating chamber 12 through the carrier gas channel.

In addition, a gas channel 41 communicates with a cross section on the opposite side (right side of FIG. 3) of an opening side of the heating chamber 12. Mixed gas M of the carrier gas C and a gas component G evolved by the heating furnace 10 (heating chamber 12) flows through the gas channel 41.

The sample holder 20 includes a stage 22 moving on the movement rail 204L attached to an inner upper surface of the attaching unit 204; a bracket 24c attached on the stage 22 and extending in a vertical direction; insulators 24b and 26 attached to a front surface (left side of FIG. 3) of the bracket 24c; a sample holding unit 24a extending from the bracket 24c in a direction of the axis O in the heating chamber 12; a sample heater 27 provided just below the sample holding unit 24a; and a sample plate 28 provided on an upper surface of the sample holding unit 24a above the sample heater 27, the sample plate on which the sample is placed.

Here, the movement rail 204L extends in a direction of the axis O (horizontal direction of FIG. 3), and the stage 22 of the sample holder 20 moves in the direction of the axis O. In addition, the opening/closing handle 22H extends in a direction perpendicular to the axis O, and is attached to the stage 22.

In addition, an upper portion of the bracket 24c has a semicircular shape and a lower portion of the bracket has a rectangular shape. Referring to FIG. 2, the insulator 24b has a substantially cylinder shape, and is provided at a front surface of an upper portion of the bracket 24c. An electrode 27a of the sample heater 27 penetrates the insulator 24b, and protrudes to an outside of the gas evolving unit. The insulator 26 has a rectangular shape, and is provided at the front surface of the bracket 24c. The insulator 26 is located lower than the insulator 24b. In addition, the insulator 26 is not provided at a lower portion of the bracket 24c, and a front surface of the lower portion of the bracket 24c is exposed to form a contact surface 24f.

The bracket 24c has a diameter slightly larger than a diameter of the heating chamber 12 such that the bracket 24c seals the heating chamber 12. The sample holding unit 24a is located in the heating chamber 12.

In addition, the sample placed on the sample plate 28 in the heating chamber 12 is heated in the heating furnace 10 such that the gas component G is evolved.

The cooling unit 30 faces the bracket 24c of the sample holder 20, and is located at an outside of the heating furnace 10 (left side of the heating furnace 10 in FIG. 3). The cooling unit 30 includes a cooling block 32 having a concave portion 32r that has a rectangular shape; cooling fins 34 connected to a lower surface of the cooling block 32; and a pneumatic cooling fan 36 connected to a lower surface of the cooling fins 34, and blowing air to the cooling fins 34.

In addition, when the sample holder 20 moves in a direction of the axis O on the movement rail 204L toward a left side of FIG. 3, and comes out of the heating furnace 10, the contact surface 24f of the bracket 24c is positioned at the concave portion 32r of the cooling block 32 by being in contact with the concave portion. Consequently, as heat of the bracket 24c is removed by the cooling block 32, the sample holder 20 (particularly, the sample holding unit 24a) is cooled.

In addition, according to the exemplary embodiment of the present invention, the sample holder 20 (including the bracket 24c) and the cooling block 32 are made of aluminum.

As shown in FIGS. 3 and 4, the splitter 40 includes the gas channel 41 connected to the heating chamber 12; a branching channel 42 connected to the gas channel 41, and opened to the outside; a mass flow controller (discharged flow rate controlling device) 42a connected to a discharge side of the branching channel 42 to control flow rate of the mixed gas M discharged from the branching channel 42 to the outside; a housing unit 43 opening the gas channel 41 therein; and a heat retaining unit 44 surrounding the housing unit 43.

As shown in FIG. 4, when viewed from the top, the gas channel 41 is connected to the heating chamber 12 and extends in a direction of the axis O and next, bends in a direction perpendicular to the axis O, and bends again in a direction of the axis O such that the gas channel reaches an end part 41e. The gas channel has a crank shape. In addition, a portion of the gas channel 41 that extends in a direction perpendicular to the axis O is provided with a center thereof having a circular shape that has a diameter larger that a diameter of the gas channel to define a branch chamber 41M. The branch chamber 41M extends to an upper surface of the housing unit 43. The branch chamber 41M is fitted with the branching channel 42 having a diameter slightly smaller than that of the branch chamber 41M.

The gas channel 41 may have a straight line shape extending in a direction of axis O from the heating chamber 12 connected with the gas channel to the end part 41e. Alternatively, depending on a positional relationship with the heating chamber 12 or with the ion source 50, the gas channel 41 may have a various curved shape, a line shape having an angle to the axis O, etc.

In addition, according to the exemplary embodiment of the present invention, the gas channel 41 has a diameter about 2 mm, and the branch chamber 41M and the branching channel 42 have respective diameters about 6 mm. In addition, a ratio (split ratio) of flow rates from the gas channel 41 to the end part 41e, and flow rates branched to the branching channel 42 is determined by a flow resistance. The mixed gas M may flow more through the branching channel 42. In addition, the split ratio is controlled by adjusting an opening ratio of the mass flow controller 42a.

As shown in FIGS. 3 and 4, the ion source 50 includes an ionizer housing unit 53; an ionizer heat retaining unit 54 surrounding the ionizer housing unit 53; a discharge needle 56; and a staying unit 55 fixing the discharge needle 56. The ionizer housing unit 53 has a plate shape, and a surface of the plate is parallel to the axis O. A small hole 53C penetrates the center of the surface of the plate. In addition, the end part 41e of the gas channel 41 passes through the ionizer housing unit 53, and faces a side wall of the small hole 53C. In the meantime, the discharge needle 56 extends in a direction perpendicular to the axis O, and faces the small hole 53C.

In addition, in the mixed gas M introduced around the small hole 53C from the end part 41e, the gas component G is ionized by the discharge needle 56.

The ion source 50 is a well-known device. According to the exemplary embodiment of the present invention, atmospheric pressure chemical ionization (APCI) is applied to the ion source. APCI causes minimal fragmentation of the gas component G, such that fragmentation peak does not occur. Therefore, it is possible to detect the measurement target without separating the gas component G by using a chromatograph, etc.

The gas component G ionized at the ion source 50 and the carrier gas C are introduced to the mass spectrometer 110, and are analyzed.

In addition, the ion source 50 is contained in the ionizer heat retaining unit 54.

Figure 5:
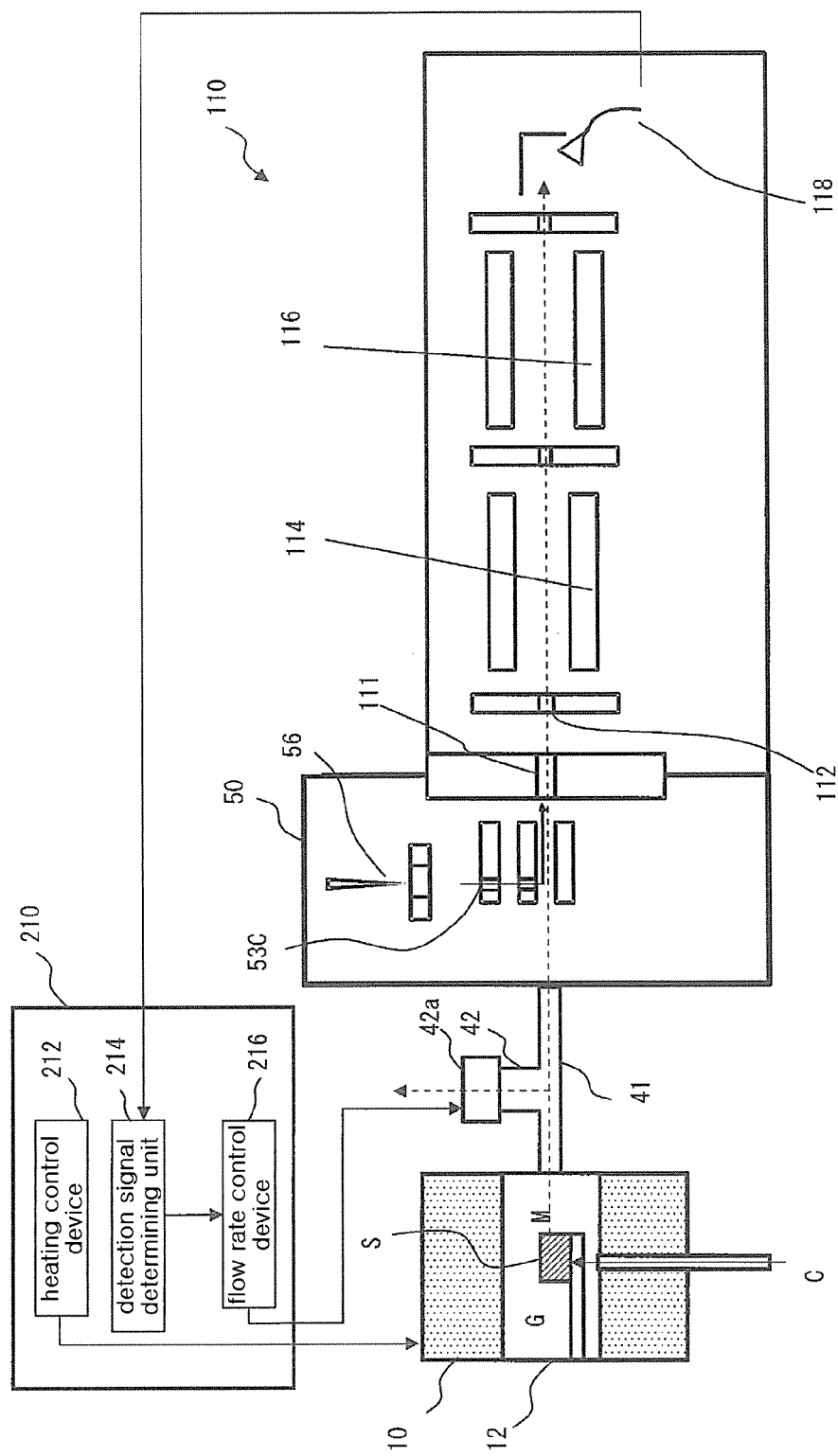
FIG. 5 is a block diagram showing a process of analyzing a gas component by the evolved gas analyzer.

FIG. 5 is a block diagram showing a process of analyzing a gas component by the evolved gas analyzer 200.

The sample S is heated in the heating chamber 12 of the heating furnace 10, and the gas component G is evolved. Heating condition (temperature rising rate, maximum temperature, etc.) of the heating furnace 10 is controlled by a heating control device 212 of the computer 210.

The gas component G is mixed with the carrier gas C introduced in the heating chamber 12 to be a mixed gas M, and the mixed gas M is introduced in the splitter 40. A detection signal determining unit 214 of the computer 210 receives a detection signal from a detector 118 of the mass spectrometer 110.

A flow rate control device 216 determines whether or not peak intensity of the detection signal received from the detection signal determining unit 214 is within a threshold range. When the peak intensity is out of the threshold range, the flow rate control device 216 controls the opening ratio of the mass flow controller 42a. Therefore, flow rate of the mixed gas M discharged from the splitter 40 to an outside through the branching channel 42 is controlled, and further, flow rate of the mixed gas M introduced from the gas channel 41 into the ion source 50 is controlled, thereby optimizing a detection accuracy of the mass spectrometer 110.

The mass spectrometer 110 includes a first fine hole 111 through which the gas component G ionized at the ion source 50 is introduced; a second fine hole 112 through which the gas component G flows, after the first fine hole 111; an ion guide 114; a quadrupole mass filter 116; and the detector 118 detecting the gas component G discharged from the quadrupole mass filter 116.

The quadrupole mass filter 116 varies an applied high frequency voltage such that mass is scanned. The quadrupole mass filter generates a quadrupole electric field, and detects ions by moving the ions like a pendulum swinging within the quadrupole electric field. The quadrupole mass filter 116 functions as a mass separator passing only gas component G within a certain mass range such that the detector 118 may identify and quantify the gas component G.

In addition, in comparison with an entire ions detection (scan) mode detecting ions of a certain range of a mass-to-charge ratio, when using a selected ion detection (SIM) mode detecting only ions of a certain mass-to-charge ratio m/z of a gas component, which is a measurement target, a detection accuracy of the gas component, which is the measurement target, increases.

Hereinafter, a method for correcting the evolved gas analyzer according to the exemplary embodiment of the present invention will be described with reference to FIG. 6.

A reference sample including a gas component as a measurement target is prepared. According to the exemplary embodiment of the present invention, the measurement target includes a plurality of gas components, and the reference sample includes the plurality of gas components (for example, diethylhexyl phthalate (DEHP), dibutyl phthalate (DBP), benzylbutyl phthalate (BBP), and diisobutyl phthalate (DIBP), that are four substances of the phtalates restricted under RoHS). Gas component contents of the reference sample are not limited. However, it is better to respectively set the gas component contents of the reference sample close to assumed gas component contents of a test sample (for example, it is desirable to set four gas component contents to the same digit numbers because RoHS limits DEHP, DBP, BBP, and DIBP at 1000 ppm). In addition, a gas component content of a sample is (mass of a gas component)/(entire mass of a sample).

Next, a correction is performed in sequence as follows.

(1) First, a mass spectrum position is corrected to be located at a reference spectrum position, the mass spectrum position corresponding to a mass-to-charge ratio m/z of a mass spectrum of each gas component of the reference sample. For example, referring to FIG. 6, in order to respectively locate mass spectrum positions of three gas components 1, 2, and 3 within allowable ranges 2L of reference spectrum positions m1, m2, and m3, settings (for example, high frequency voltage) of the mass spectrometer (quadrupole mass filter 116) 110 are adjusted.

Figure 7:
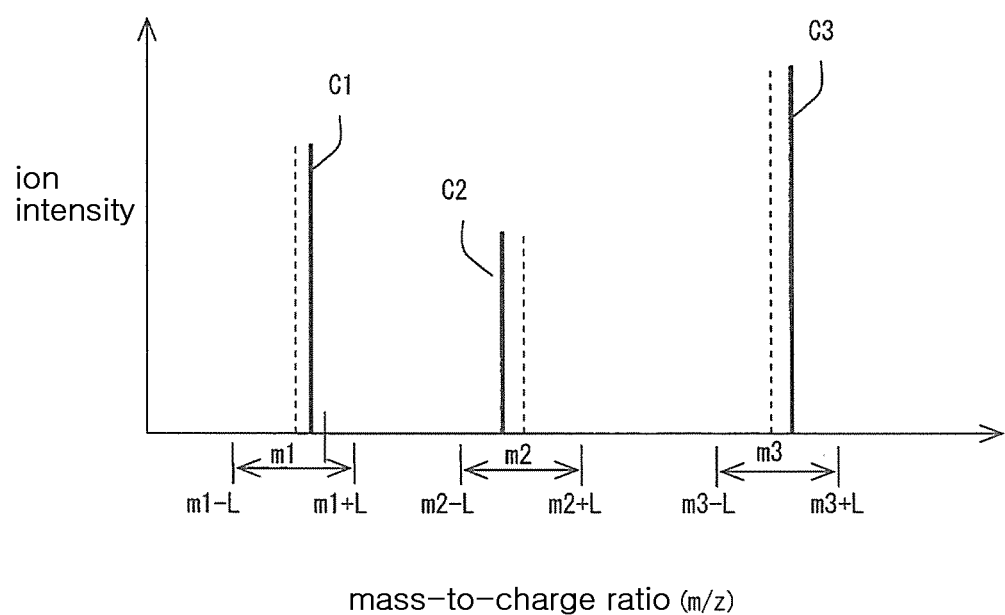
FIG. 7 is a view showing the method for analyzing evolved gas according to the exemplary embodiment of the present invention.

In addition, as shown in FIG. 7, an allowable range 2L is a range within ±L of each of reference spectrum positions m1, m2, and m3. It is desired that the mass spectrum positions of gas components of the reference sample are located within respective allowable ranges 2L. According to the exemplary embodiment of the present invention, kind of each the gas components in the reference sample are predetermined. Therefore, unlike a general-purpose analysis using undefined measurement targets, it is not necessary to perform an adjustment minimizing differences between the mass spectrum positions and the reference spectrum positions of multiple gas components. However, a method of correcting the mass spectrum positions to be located at respective reference spectrum positions is not limited thereto, and the adjustment may be performed.

As described above, it is possible to correct detection sensitivity differences in analysis devices, day-to-day variations thereof, etc. relative to the mass spectrum positions of the gas components, thereby precisely obtaining chromatograms of the gas components that will be described hereinafter.

(2) Second, after the correcting of the mass spectrum position, a sensitivity correction factor $Cs=Ss/S$ is calculated by using an area S and a reference area Ss of a chromatogram showing an intensity (ion intensity) of the gas component of the reference sample at a retention time, the sensitivity correction factor Cs being used to measure an area of a chromatogram of the gas component of the test sample. Cs is a correction factor when measuring an area of a chromatogram of the gas component of the test sample. The area S of the chromatogram is influenced by degradation of the ion source ionizing the gas components, measured temperature, etc. Therefore, the sensitivity correction factor is required to be used.

Figure 6:
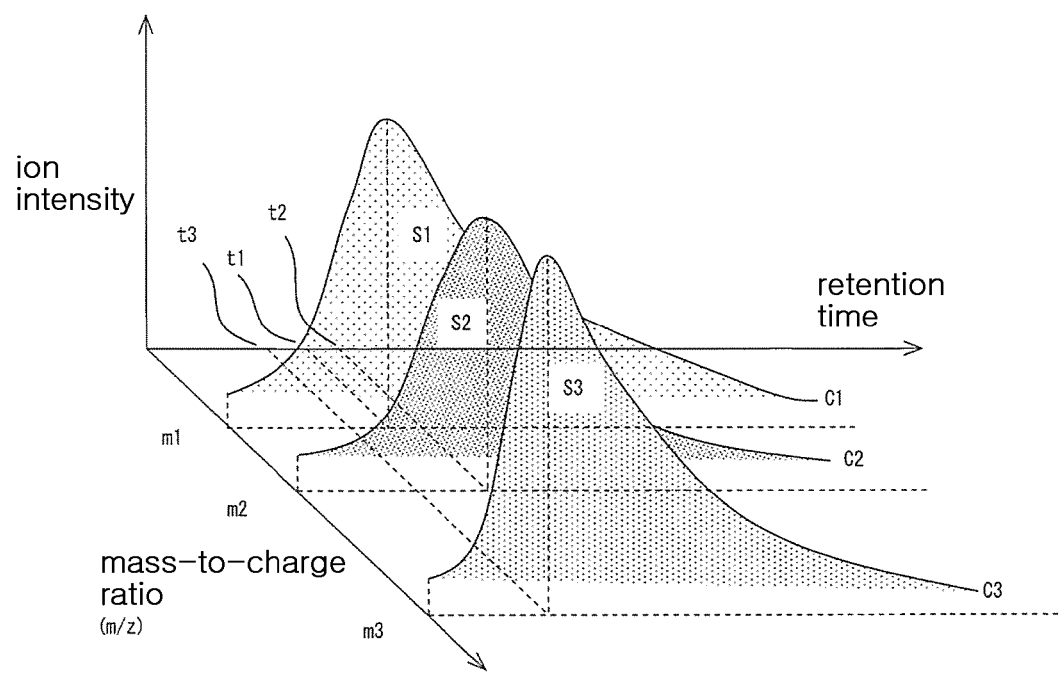
FIG. 6 is a view showing a method for analyzing evolved gas according to the exemplary embodiment of the present invention.

For example, referring to FIG. 6, chromatograms C1, C2, and C3 of the three gas components 1, 2, and 3 are obtained, and a CPU of the computer 210 calculates areas S1, S2, and S3 of the chromatograms C1, C2, and C3. In the meantime, reference areas Ss1, Ss2, and Ss3 of the gas components 1, 2, and 3 are stored in the memory unit of the computer 210. Therefore, the CPU calculates Cs of each of the gas components 1, 2, and 3 (for example, in the case of gas component 1, Cs1=Ss1/S1). An area value is regarded as Cs1 multiplied by an area of a chromatogram of the actual gas component 1 of the test sample. It is possible to precisely quantify the gas component 1 by using the area value.

(3) Third, a heating correction factor H=t/ts is calculated by using a time t indicating a maximum peak of each of the chromatograms C1, C2, and C3, and a reference time ts, the heating correction factor being used to correct a heating rate of the test sample in the heating furnace 10 (actually, on the sample plate 28 monitoring temperature). H is a heating correction factor that is used to correct a heating rate of the test sample in the heating furnace 10, when measuring the gas component of the test sample. In the case of heating the test sample, when the heating rate (temperature rising rate) varies, the shape of chromatogram (time t indicating a maximum peak) also varies, and thus, the area of the chromatogram varies. Therefore, the heating correction factor is required to be used.

For example, referring to FIG. 6, the CPU calculates times t1, t2, and t3 of the chromatograms C1, C2, and C3. In the meantime, reference times ts1, ts2, and ts3 of the gas components 1, 2, and 3 are stored in the memory unit of the computer 210. Accordingly, the CPU calculates H=t/ts of each of the gas components 1, 2, and 3.

In order to measure the chromatogram C1 of the test sample, the heating condition of the heating furnace 10 is properly controlled by using the heating correction factor H, thereby obtaining a precise chromatogram. In addition, an actual area value is calculated by multiplying the sensitivity correction factor Cs1 of the gas component 1 obtained in above (2) by an area of the chromatogram about the gas component 1 of the test sample. Therefore, it is possible to precisely quantify the gas component 1. Consequently, it is possible to correct heating performances of the heating furnace 10 or of the sample heater 27 of the evolved gas analyzer 200, measured temperature, detection sensitivity differences in analysis devices, day-to-day variations thereof, etc. by using the reference sample. In addition, a measurement accuracy (particularly, area of chromatogram) may increase.

Specifically, the heating unit heater 14a controls the temperature in the heating furnace 10 to be uniformly maintained at a certain temperature. The sample heater 27 provided under the sample plate 28 monitors the temperature of the sample using its resistance, and controls the heating rate of the sample based on the monitored temperature of the sample. Therefore, [correcting the heating rate of the sample in the heating furnace] means that correcting the heating rate of a part (the sample heater 27 in this embodiment) controlling heating condition based on the temperature of the sample.

Here, when the measurement target includes a plurality of gas components, H=Σai×ti/tsi is calculated. A natural number indicating a gas component i is denoted as i, for example, gas components 1, 2, and 3. A well-known heating sensitivity factor of the gas component i is denoted as ai indicating that peak times (time t indicating a maximum peak) of the gas components easily vary depending on variations in the heating rate. According to the exemplary embodiment of the present invention, ai is heating sensitivity factors a1, a2, and a3 of the gas components 1, 2, and 3. A reference time indicating the maximum peak of the chromatogram of the gas component i is denoted as tsi. According to the exemplary embodiment of the present invention, tsi is reference times ts1, ts2, and ts3 indicating maximum peaks of the chromatograms C1, C2, and C3 of the gas components 1, 2, and 3.

Therefore, the heating correction factor is H=(a1×t1/ts1)+(a2×t2/ts2)+(a3×t3/ts3).

Figure 8:
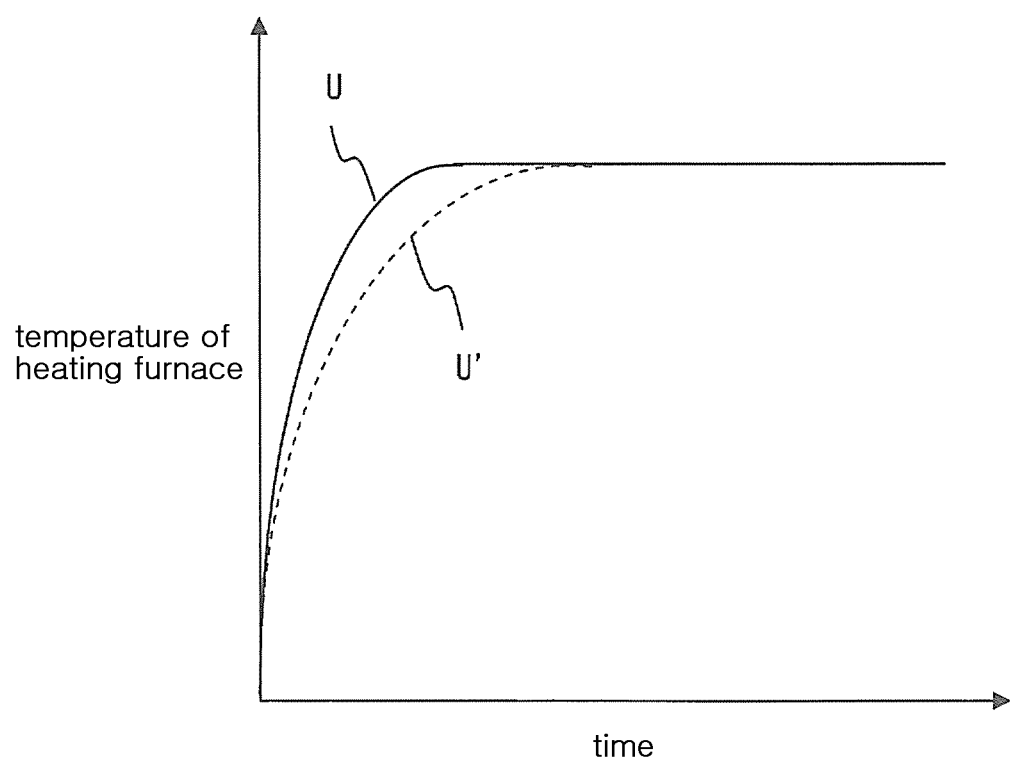
FIG. 8 is a view showing an example of correcting a heating rate of a test sample in a heating furnace by using a heating correction factor H.
Figure 9:
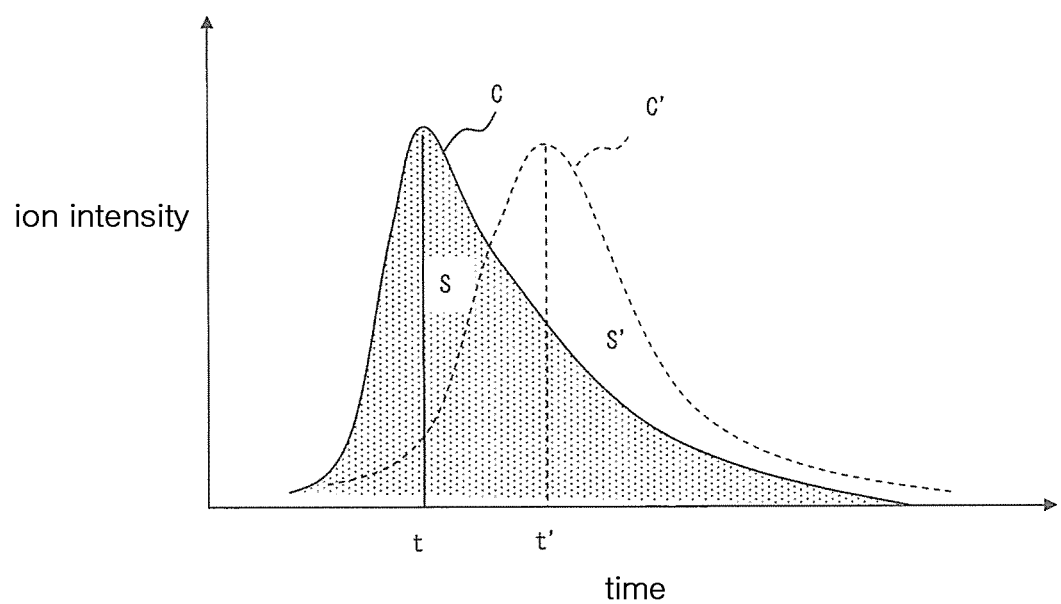
FIG. 9 is a view showing a shape change in a chromatogram caused by the heating rate of the test sample when performing mass spectrometry.

FIG. 8 is a view showing an example of correcting the heating rate of the test sample in the heating furnace 10 by using the heating correction factor H. For example, when the time t indicating maximum peak of the test sample is less than the reference time is (H<1), the heating rate is excessive. The heating rate is required to be lower than an original heating pattern U. Therefore, the heating rate is corrected as a lower heating pattern U' by multiplying the heating correction factor H by a gradient (heating rate) of an original heating program.

Generally, when the heating rate of the sample heater 27 is too fast, gas concentration of the gas component rapidly increases. Therefore, ionizing efficiency of the ion source cannot follow the increase, and thus, a peak area value decreases. That is, it is possible to obtain a precise chromatogram by correcting the heating rate as the lower heating pattern U'.

In the case that the correction processing unit 210 automatically operates the above-described processes (1) to (3), it operates as follow.

(1) First, the detection signal determining unit 214 adjusts the settings (for example, high frequency voltage) of the mass spectrometer (quadrupole mass filter 116) 110 based on the received detection signal, in order to respectively locate the mass spectrum positions of three gas components 1, 2, and 3 within allowable ranges 2L of reference spectrum positions m1, m2, and m3 stored in the memory unit.

(2) Second, the detection signal determining unit 214 calculates the sensitivity correction factor Cs, based on the received detection signal and the reference areas Ss1, Ss2, and Ss3 stored in the memory unit. The calculated sensitivity correction factor Cs is stored in the memory unit.

(3) Third, the detection signal determining unit 214 calculates the heating correction factor H=t/ts based on the received detection signal and the reference time is stored in the memory unit. The calculated heating correction factor H is stored in the memory unit.

Next, when performing mass spectrometry on the gas components of the test sample, the heating control device 212 corrects the heating rate of the test sample in the heating furnace 10 by controlling the sample heater 27 based on the heating correction factor H and performs measurement in this state. In addition, the detection signal determining unit 214 outputs an actual area value calculated by multiplying the sensitivity correction factor Cs1 by an area of the chromatogram of the test sample.

It should be understood that the exemplary embodiment according to the concept of the present invention is not limited to the exemplary embodiment, but various modifications, equivalents, additions and substitutions are possible, without departing from the scope and spirit of the invention.

Besides phtalates, the measurement target may be brominated flame retardants (polybrominated biphenyl (PBB), polybrominated diphenyl ether (PBDE)) restricted under RoHS, without being limited thereto.

Components, shapes, configurations, etc. of the heating furnace, the ion source, and the mass spectrometer are not limited to the exemplary embodiment. In addition, a method of correcting the mass spectrum positions to be located at respective reference spectrum positions is not limited to the exemplary embodiment, and a conventional method may be used.

In addition, the evolved gas analyzer may be provided with an autosampler automatically continuously supplying a sample into the heating unit. The autosampler may be provided with a certain position holding the reference sample. The reference sample is analyzed once in advance of operating the method for correcting the evolved gas analyzer. Consequently, the method for correcting the evolved gas analyzer (1) to (3) may be automatically operated.

What is claimed is:

1. A method for correcting an evolved gas analyzer analyzing evolved gas by using a mass spectrometer which detects a gas component evolved by heating a sample including the gas component as a measurement target through performing mass analysis of an ion generated by ionizing the gas component, the method comprising:

correcting a mass spectrum position to match a reference spectrum position, the mass spectrum position corresponding to a mass-to-charge ratio m/z of a mass spectrum obtained as to the gas component of the reference sample;

after the correcting the mass spectrum position, calculating a sensitivity correction factor $C_s=S_s/S$ at the time an area of a chromatogram of the gas component of the actual sample is measured from an area S, showing an intensity with respect to a retention time obtained as to the gas component of the reference sample, and a reference area $S_s$ of a chromatogram; and calculating a heating correction factor $H=t/t_s$, correcting a heating rate of the sample in a heating unit evolving the gas component by heating the sample at the time the gas component of the sample is measured, from a time t, indicating a maximum peak of the chromatogram, and a reference time $t_s$.

2. The method of claim 1, wherein the measurement target comprises a plurality of the gas components and the heating correction factor to be calculated is $H=\Sigma a_i \times t_i/t_{si}$ (i: a natural number indicating a gas component i, $a_i$: a known heating sensitivity coefficient of the gas component i, $t_i$: a time indicating a maximum peak of a chromatogram of each gas component i, and $t_{si}$: a reference time indicating the maximum peak of the chromatogram of each gas component i).

3. An evolved gas analyzer, comprising:

a heating unit evolving a gas component by heating a sample;

an ion source generating ions by ionizing the gas component evolved by the heating unit;

a mass spectrometer detecting the gas component by performing mass analysis of the ions; and a correction processing unit, comprising a computer consisting of a processor and a non-transitory storage medium which stores a series of executable instructions which, when executed by the processor, cause the processor to perform calculations of all of the following:

using a reference sample including the gas component as a measurement target, correcting a mass spectrum position to match a reference spectrum position, the mass spectrum position corresponding to a mass-to-charge ratio m/z of a mass spectrum obtained as to the gas component of the reference sample;

after correcting the mass spectrum position, calculating a sensitivity correction factor $C_s=S_s/S$ at the time an area of a chromatogram of the gas component of the actual sample is measured from an area S, showing an intensity with respect to a retention time obtained as to the gas component of the reference sample, and a reference area $S_s$ of a chromatogram; and calculating a heating correction factor $H=t/t_s$, correcting a heating rate of the sample in the heating unit at the time the gas component of the actual sample is measured, from a time t, indicating a maximum peak of the chromatogram, and a reference time $t_s$.

* * * * *